United States Patent [19]

Son et al.

[11] 4,455,401

[45] Jun. 19, 1984

[54] 2-KETO-DIAZACYCLOALKANE-URETHANE OLIGOMERS AND U-V LIGHT STABILIZED COMPOSITIONS

[75] Inventors: Pyong N. Son, Akron; John T. Lai, Broadview Heights, both of Ohio

[73] Assignee: The B. F. Goodrich Company, Akron, Ohio

[21] Appl. No.: 375,242

[22] Filed: May 6, 1982

[51] Int. Cl.³ .................. C08K 5/34; C07D 243/08; C07D 241/08
[52] U.S. Cl. ........................ 524/91; 524/98; 524/100; 524/102; 544/358; 544/384
[58] Field of Search ............ 544/358, 321, 384; 524/92, 100, 98, 91, 102

[56] References Cited

U.S. PATENT DOCUMENTS

| | | | |
|---|---|---|---|
| 4,190,571 | 2/1980 | Lai et al. | 524/100 |
| 4,292,240 | 9/1981 | Lai et al. | 544/231 |
| 4,297,497 | 10/1981 | Lai | 544/384 |

*Primary Examiner*—John Kight, III
*Assistant Examiner*—Kriellion Morgan
*Attorney, Agent, or Firm*—Alfred D. Lobo; Nestor W. Shust

[57] ABSTRACT

Novel compounds have been discovered in which a bis compound of a polysubstituted 2-keto-1,4-diazacycloalkane ("2KDZC") provides a bridge between diisocyanate groups so as to form an oligomeric 2KDZC-urethane ("2K-U" oligomer) having from 2 to about 15 repeating units. The bis compound bridge itself consists essentially of two distally linked polysubstituted 2KDZC moieties, and the 2K-U oligomer formed consists essentially of two 2KDZC moieties linked through their $N^1$ atoms, which moieties in turn are distally linked to urethane groups through the $N^4$ atoms of the 2KDZC. Such 2K-U oligomers unexpectedly contain a self-limiting number of 2K-U repeating units which happens to provide 2K-U oligomers which are desirable and highly effective u-v light stabilizers in organic materials. More specifically, this invention provides a novel class of polymeric hindered amine-urethane derivatives, particularly piperazinone bis compounds which may be distally linked to each other in a single step reaction utilizing an appropriately substituted diamine, a haloform such as bromoform or chloroform, in one of several known syntheses for making 2-keto-diazacycloalkanones, some of which syntheses may preferably utilize a phase transfer catalyst. This bis compound may then be hydroxyalkylated and reacted with an appropriate diisocyanate.

9 Claims, No Drawings

2-KETO-DIAZACYCLOALKANE-URETHANE OLIGOMERS AND U-V LIGHT STABILIZED COMPOSITIONS

BACKGROUND OF THE INVENTION

Organic materials, whether natural or synthetic, are conventionally protected against degradation by ultraviolet (UV) light by incorporating a UV light stabilizer in the material. Many classes of compounds are known to be useful UV light stabilizers, some being more effective than others. Particularly effective 2-keto-diazacycloalkanes which provide stabilized compositions resistant to degradation by UV light, include the 2-keto-1,4-diazacycloalkanes disclosed in U.S. Pat. No. 4,190,571; and, the 2-keto-1,5-diazacycloalkanes disclosed in U.S. Pat. No. 4,207,228. Other 2-keto-diazacycloalkanes useful as UV light stabilizers are disclosed in U.S. Pat. Nos. 3,919,234; 3,920,659; and 3,928,330 which teach substituted piperazinediones. Cycloalkanes useful as UV light stabilizers are disclosed in Ger. Offen. No. 2,315,042; Japanese Pat. Nos. 7,453,571 and 7,453,572.

The compounds of this invention belong to a the general class of compounds known as hindered amines. Hindered amines, to which general class the compounds of the invention belong, are known to have utility as u-v light stabilizers in synthetic resins subject to actinic radiation. However, not all hindered amines are effective stabilizers against u-v light degradation in normally solid polymers. Some hindered amines are thermally unstable at as low as 100° C. which precludes their use in any organic material which is processed at or above that temperature. Further, particularly with polysubstituted heterocyclic ring compounds, N atoms in the ring are known to have a beneficial effect but there is no logical reason to expect that an oligomer may be formed which has relatively few repeating units of a polyisocyanate which are self-limiting to just about the right number so as to provide a desirable molecular weight; nor is there any reason to expect that a peculiar structure of two distally linked polysubstituted 2-keto-1,4-diazacycloalkane ("2KDZC") moieties, themselves distally linked, would, in conjunction with a polymeric isocyanate, provide better stabilization activity than either the 2KDZC Bis compound, or the polymeric isocyanate (also termed "urethane oligomer"). By "distally linked" we refer to bridging or linking by at least 2 carbon atoms.

Because of the unpredictability of the effectiveness of various hindered amines solely based on their (hindered) structure, much effort has been expended to synthesize hindered amines which must then be tested for possible utility as u-v light stabilizers. One of the synthesis is described in an article titled "Hindered Amines. Novel Synthesis of 1,3,3,5,5-Pentasubstituted 2-Piperazinones" by John T. Lai in J. Org. Chem. 45, 754 (1980).

Hindered amines of the prior art are generally complex compounds not prepared with notable ease, and their properties, particularly their compatibility in various synthetic resins, is difficult to predict. Apparently small differences in structure, result in large differences in performance. Prolonged efforts to provide simpler compounds which are relatively easily prepared, have resulted in the 2-keto-1,4-diazacycloalkanes and the 2-keto-1,5-diazacycloalkanes disclosed in U.S. Pat. Nos. 4,190,571 and 4,207,228.

The key to the ubiqutous presence of "hindered amine" u-v light stabilizers is the relative ease with which they are commercially prepared, compared with u-v stabilizers having comparable activity but different structures. Currently available, relatively easily prepared u-v stabilizers include for example, Tinuvin ®622 which is a succinate ester of a polysubstituted piperidine, more fully disclosed in U.S. Pat. Nos. 4,233,410 and 4,233,412; Tinuvin ®770 which is a triazine substituted with piperidine substituents; and, Chimasorb ®944 which has a polytriazine structure with piperidine substituents, as disclosed in U.S. Pat. No. 4,086,204. However, the aforementioned stabilizers are relatively easily extracted from prior art u-v stabilized compositions. This invention derives from the discovery that changes in structure of a hindered amine are effective to improve not only the ease with which they may be prepared and thus be inexpensive, but also to improve their extraction from organic polymers, thus giving the polymers longer lasting protection against degradation by u-v light.

The present invention further derives from research in the field of the synthesis of hindered amines having peculiar structural characteristics, and an evaluation of their effectiveness as u-v light stabilizers. The concept of retaining the "2-keto" ring structure of a heterocyclic ring containing at least one N atom was the basis upon which the search for effective polymers containing this structure was initiated. The practicality of providing more than two substituents on the N-adjacent C atoms of a 2-keto-1,4-diazacycloalkane derives from the discovery of the "ketoform synthesis" disclosed in U.S. Pat. No. 4,167,512; the "cyanohydrin acetate synthesis" disclosed in U.S. Pat. No. 4,240,961; and, the "soft ion catalyst synthesis" disclosed in U.S. Pat. No. 4,246,412; other preparations of 2-keto-1,4-diazacycloalkanes, particularly bis compounds thereof, disclosed in U.S. Pat. Nos. 4,190,571; 4,292,240; 4,297,497; and 4,309,336 inter alia; and the disclosures of each of the foregoing patents are incorporated by reference thereto as if fully set forth herein. The retention of the 2-keto structure in a diazacycloalkane bis compound which links at least two urethane moieties, spurred the discovery of the novel polysubstituted 2-keto-1,4-diazacycloalkane-urethane ("2K-U" for brevity) oligomers of this invention as highly effective u-v stabilizers in novel compositions.

SUMMARY

Novel compounds have been discovered in which a bis compound of a polysubstituted 2-keto-1,4-diazacycloalkane ("2KDZC") provides a bridge between diisocyanate groups so as to form an oligomeric 2KDZC-urethane ("2K-U" oligomer) having from 2 to about 15 repeating units. More specifically, the bis compound bridge itself consists essentially of two distally linked polysubstituted 2KDZC moieties.

It is therefore a general object of this invention to provide novel 2K-U oligomers in which two polysubstituted 2KDZC molecules are distally linked by a first connecting link ("2KDZC link") consisting essentially of a group selected from polymethylene having from 2 to 12 carbon atoms, xylenyl and phenyl; and, each of which 2KDZC molecules is in turn distally linked by a second connecting link ("2K-U link") to a difunctional urethane unit having the structure

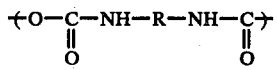

wherein, R is selected from the group consisting of alkylene having from 2 to 12 carbon atoms, toluyl, diphenylmethyl, naphthyl, dimethyl-biphenyl, dimethoxy-biphenyl, methylcyclohexyl, dicyclohexylmethyl, xylyl, isophoronyl, trimethylhexyl, and the like; and, 'n' is an integer in the range from about 1 to about 5 so as to form, with the 2K-U bis compound, a polymeric 2K-U ("2K-U oligomer").

Further, it has been discovered that a 2K-U oligomer may be formed which consists essentially of two 2KDZC moieties linked through their $N^1$ atoms, which moieties in turn are distally linked to a urethane through the $N^4$ atoms of the 2KDZC. Such 2K-U oligomers unexpectedly contain a self-limiting number, from about 1 to about 5, of 2K-U repeating units which happens to provide 2K-U oligomers which are desirable and highly effective u-v light stabilizers in organic materials.

It is therefore a general object of this invention to provide novel u-v light stabilized compositions containing 2K-U oligomers of this invention.

It is a specific object of this invention to provide a novel class of oligomeric hindered amine-urethane derivatives useful as u-v light stabilizers for polyolefins and other light degradable polymers which derivatives are characterized by having (a) at least two polysubstituted 2KDZC molecules distally linked to each other and also distally linked to urethane groups, and, (b) improved resistance to extraction from such polymers in prolonged contact with an aqueous solution.

It is a more specific object of this invention to provide a novel class of piperazinone bis compounds which may be distally linked to each other in a single step reaction utilizing an appropriately substituted diamine, a haloform such as bromoform or chloroform, in one of several known syntheses for making 2-keto-diazacycloalkanones, some of which syntheses may preferably utilize a phase transfer catalyst.

DETAILED DESCRIPTION OF PREFERRED EMBODIMENTS

The basic structure of the stabilizer compounds used in stabilized compositions of this invention, is a bis compound comprising two polysubstituted 2KDZC moieties linked through their $N^1$ atoms which bis compound in turn links a urethane group through each of the other N atoms of the diazacycloalkanes. The resulting 2K-U oligomer has the structure:

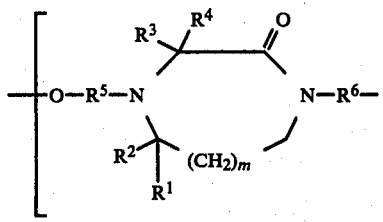

-continued

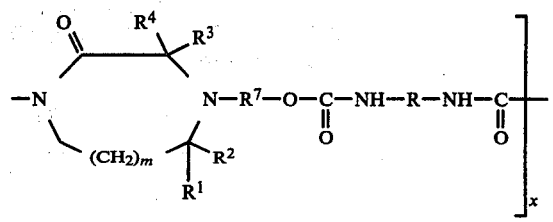

wherein, m represents an integer in the range from 0 to 5, being the number of methylene groups forming a bridge of variable length between the ring N atoms, and some of which groups (a) together with the carbons to which they are bound, may form a cyclopentyl, cyclohexyl or cycloheptyl endo ring, or (b) be substituted; so that, when m is 0, the 2KDZC moiety is a piperazinone ring; when m is 1 the 2KDZC moiety is a 5-keto-1,4-diazacycloheptane (referred to herein as a "diazepinone") ring; when m is 4 and cyclized with the other two contiguous C atoms (in the bridge between the N atoms) to form an endo ring, the 2KDZC moiety is decahydroquinoxalinone;

x represents an integer in the range from 2 to about 15;

R is selected from the group consisting of alkylene having from 2 to about 12 carbon atoms, toluyl, diphenylmethyl, naphthyl, dimethylbiphenyl, dimethoxy-biphenyl, methylcyclohexyl, dicyclohexylmethyl, xylyl, isophoronyl, trimethylhexyl;

$R^1$, $R^2$, $R^3$ and $R^4$ are independently selected from the group consisting of hydrogen, aryl, alkyl having from 1 to about 24 carbon atoms, cycloalkyl having from 5 to about 7 carbon atoms, aralkyl having from 7 to about 20 carbon atoms, cyanoalkyl having from 2 to about 12 carbon atoms, ether having from 4 to about 18 carbon atoms, and hydroxyalkyl having from 1 to about 18 carbon atoms;

$R^1$ and $R^2$ together, or $R^3$ and $R^4$ together, or each pair, may be cyclized forming a ring having from about 5 to about 8 carbon atoms;

except that not more than one of $R^1$, $R^2$, $R^3$ or $R^4$ may be hydrogen, and no more than three of $R^1$, $R^2$, $R^3$ and $R^4$ may be cyclic;

$R^5$ and $R^7$ are each polymethylene having from 2 to about 12 carbon atoms each of which polymethylene constitutes a connecting link distally connecting a 2-keto-diazacycloalkane moiety to a urethane group; and, $R^6$ is selected from the group consisting of polymethylene having from 2 to about 12 carbon atoms, xylenyl and substituted or unsubstituted phenyl, which group is a connecting link distally connecting one 2-keto-1,4-diazacycloalkanes moiety to another such moiety.

It is especially significant that these relatively high molecular weight compounds contain a polysubstituted 2KDZC bis compound distally linked to a urethane, and that groups may be independently substituted in both the 2KDZC bis compound or the urethane group, to produce stabilizers having not only desirable uv light stabilizing properties, but also heat stabilizing properties complemented with suitable solubility and dispersability. The polysubstituted 2KDZCs together with the urethane group linked thereto are referred to herein as "2K-U oligomers" because they are polymers having from 2 to about 15 repeating units.

It is even more significant that an alkoxylated 2KDZC bis compound may be used as a bridge between urethane oligomers having a self-limiting number of urethane repeating units. If the number were not self-limiting in the range from 1 to about 10, and more preferably in the range from 2 to about 5, the 2K-U oligomer would not be easily dispersable in an organic polymer and therefore be of little use as a u-v stabilizer. The self-limiting property of the 2K-U oligomer is attributable to the steric hindrance effects of the substituents on the $N^4$ atoms of the 2KDZC, and also to the relative impurity of the hydroxyalkylated bis compound which is not especially purified before reacting it with a preselected diisocyanate.

The polysubstituted 2K-U compounds are generally oils or high melting crystalline solids soluble in acetone, diethyl ether, dioxane, tetrahydrofuran, carbon tetrachloride, chloroform, lower primary alcohols having from 1 to about 5 carbon atoms such as methanol, ethanol and propanol, aromatic hydrocarbons such as benzene and toluene, but much less soluble in aliphatic hydrocarbons such as hexane. 2K-U oligomers are generally insoluble in water; they range in color from white to straw-colored when pure.

The amount of 2K-U stabilizer employed will vary with the particular material to be stabilized and also the particular substituents in the 2K-U employed. Generally however, for effective uv light stabilization of organic materials, an amount of the 2K-U used is in the range from about 0.001 percent to about 10 percent by weight (% by weight) based on the weight of organic material. In typical stabilized compositions the amount of substituted PIP-T used is in the range from about 0.01 to about 5% by weight.

Compositions of this invention are synthetic resinous materials which have been stabilized to combat the deleterious effects of uv light, thermal or oxidative degradation such as are usually evidenced by discoloration and/or embrittlement. These compositions generally benefit from the inclusion of additional, secondary stabilizers to achieve even greater stability against a combination of actinic light, heat and oxygen. Therefore, in conjunction with the stabilizers of this invention, compositions may include stabilizers against degradation by heat and/or oxygen which secondary stabilizers may be present in the range from about 0.1 part to about 10 parts by weight, and preferably from about 0.2 part to about 5 parts by weight per 100 parts by weight of the organic continuous phase. Several types of known UV secondary stabilizers may be used, such as those disclosed in U.S. Pat. Nos. 3,325,448; 3,769,259; 3,920,659; 3,962,255; 3,966,711; 3,971,757; inter alia.

Organic materials which may be stabilized against uv light, thermal and oxidative degradation, include copolymers of butadiene with acrylic acid, alkyl acrylates or methacrylates, polyisoprene, polychloroprene, and the like; polyurethanes, vinyl polymers known as PVC resins such as polyvinyl chloride, copolymers of vinyl chloride with vinylidene chloride, copolymers of vinyl halide with butadiene, styrene, vinyl esters, and the like; polyamides such as those derived from the reaction of hexamethylene diamine with adipic or sebacic acid; epoxy resins such as those obtained from the condensation of epichlorohydrin with bisphenols, and the like; ABS resins, polystyrene, polyacrylonitrile, polymethacrylates, poly-carbonates, varnish, phenol-formaldehyde resins, polyepoxides, polyesters, and polyolefin homo- and copolymers such as polyethylene, polypropylene, ethylene-propylene polymers, ethylene-propylenediene polymers, ethylene-vinyl acetate polymers, and the like. The substituted 2K-U compounds can also be used to stabilize mixtures and blends of polymeric materials such as ABS resin blends, PVC and polymethacrylate blends, and blends of polyolefin homopolymers and copolymers such as blends of polypropylene in epdm polymers.

Most preferred are polysubstituted 2K-U oligomers of this invention having two polysubstituted piperazinones distally linked together through their $N^1$ atoms, and again distally linked through their $N^4$ atoms to urethane groups, so as to form 2K-U oligomers having from 2 to about 15 repeating units. Such 2K-U oligomers are especially useful as uv-light-stabilizers for synthetic resinous materials which are at least partially permeable to visible light, and particularly for those which are transparent thereto, such as the polyvinylaromatics and polyolefins.

Many known compounding ingredients may be used along with the polysubstituted 2K-U stabilizers in the compositions. Such ingredients include metal oxides such as zinc, calcium and magnesium oxide, fatty acids such as stearic and lauric acid, and salts thereof such as cadmium, zinc and sodium stearate and lead oleate; fillers such as calcium and magnesium carbonate, calcium and barium sulfates, aluminum silicates, asbestos, and the like; plasticizers and extenders such as dialkyl and diaryl organic acids like diisobutyl, diisooctyl, diisodecyl, and dibenzyl oleates, stearates, sebacates, azelates, phthalates, and the like; ASTM type 2 petroleum oils, paraffinic oils, castor oil, tall oil, glycerin and the like.

Particularly desirable secondary stabilizers are one or more antioxidants used in the range from about 0.1 part to about 20 parts by weight, preferably from about 0.2 part to about 5 parts by weight per 100 parts by weight of the material. Of the types of antioxidants to be used, are phosphite, phosphate, sulfide and phenolic antioxidants, the last being preferred. Most preferred are phenolic antioxidants such as 2,6-di-t-butyl paracresol; 2,2'-methylene-bis-(6-t-butyl-phenol); 2,2'-thio-bis-(4-methyl-6-t-butyl-phenol); 2,2'-methylene-bis-(6-t-butyl-4-ethyl-phenol); 4,4'-butylene-bis-(6-t-butyl-m-cresol); 2-(4-hydroxy-3,5-di-t-butylamino)-4,6-bis-(octylthio)-1,3,5-triazine; hexahydro-1,3,5-tris-(3,5-di-t-butyl-4-hydroxyphenyl)-propionyl-s-triazine; hexahydro-1,3,5-tris-(3,5-di-t-butyl-4-hydroxybenzyl)isocyanurate; tetrakis[methylene-3-(3',5'-di-t-butyl-4'-hydroxyphenyl)propionate]methane; and other antioxidant synergists such as distearyl thiodipropionate; dilauryl thiodipropionate; tri(nonylphenyl)phosphite; tin thioglycolate; and particularly commercially available antioxidants such as Goodrite ®3114, and 3125, Irganox 1010, 1035, 1076 and 1093. Other ingredients such as pigments, tackifiers, flame retardants, fungicides, and the like may also be added.

The polysubstituted 2K-U stabilizers, and the other compounding ingredients if used, can be admixed with organic materials using known mixing techniques and equipment such as internal mixing kettles, a Banbury mixer, a Henschel mixer, a two-roll mill, an extruder mixer, or other standard equipment, to yield a composition which may be extruded, pressed, blowmolded or the like into film, fiber or shaped articles. Usual mixing times and temperatures can be employed which may be determined with a little trial and error for any particular composition. The objective is to obtain intimate and uniform mixing of the components. A favorable mixing procedure to use when adding a polysubstituted 2K-U to an organic material is either to dissolve or suspend the compound in a liquid such as hexane or benzene before adding it, or to add the 2K-U directly to the polymeric organic material whether the 2K-U is in the form of a powder or oil, or to extruder-mix the 2K-U and the polymeric material prior to forming the product.

The u-v stability of a particular composition containing a polymeric material and a polysubstituted 2K-U can be evaluated by exposing a prepared sample of the composition to Xenon or carbon arc light in a Weather-O-meter operating at a temperature of, for example, about 140° F. (60° C.) Degradation of the sample can be followed by periodically measuring tensile strength left, and the hydroperoxide absorption band at 3460 cm$^{-1}$ or carbonyl absorption band at 1720 cm$^{-1}$ using an IR spectrophotometer. The rapid formation of carbonyl indicates failure of the sample. The test procedure is well known, and is published in the text *Photodegradation, Photo-oxidation and Photostabilization of Polymers* by Ranby and Rabek, John Wiley & Sons, N.Y., N.Y. (1975), at pages 129 et seq., and is disclosed in U.S. Pat. No. 3,909,493. Failure of the sample is also checked by visual signs of cracking when the sample is bent 180°. Another convenient test for the effect of the presence of the stabilizer is measuring the hours of exposure to u-v light after which the sample retains only 50% of its original tensile strength. This test is used to evaluate the activity of various stabilizers prepared in the examples set forth hereinafter, results of the tests being set forth in Table I hereunder.

Samples of u-v stabilized compositions can also be checked for oxidative and thermal stability by measuring the time to discoloration and/or embrittlement of the sample after aging in an air circulating oven at 140° C., and other standard ASTM tests.

EXAMPLE 1

Preparation of 1,1'-(1,2-ethanediyl)bis(3,3,5,5-tetramethyl-2-piperazinone) also identfied as 1,2-ethane-bis-(N$^1$-3,3,5,5-tetramethyl-2-piperazinone) represented by the structure

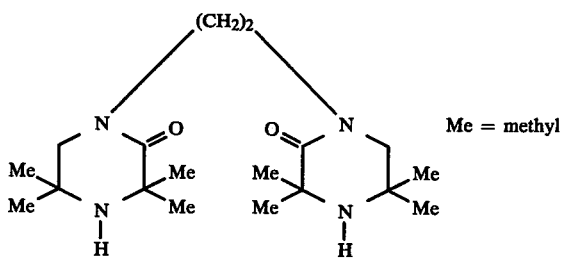

Place 9.0 g N,N$^1$-(2-amino-2-methylpropyl)-ethylene diamine and 100 ml chloroform in a 500 ml flask, and add 11.4 g acetone cyanohydrin and 1.0 g BTAC. While stirring in an ice-bath, 30 ml 50% NaOH is added dropwise in 30 min. The reaction mixture is stirred overnight at room temperature, then water is added until all the solids are dissolved. The liquid layers are separated and the aqueous layer is extracted with 50 ml chloroform. The chloroform solutions are combined and washed with water several times, then dried and concentrated. Upon distillation at 155°–165° C. under 0.2 mm Hg, an oil is obtained which when triturated with hexanes, yields about 3 g of a light yellow solid having a m pt. of 132°–4° C. The structure of the solid is confirmed by IR, GC, NMR and mass spectrometer data as that given immediately hereinabove.

EXAMPLE 2

Preparation of 1,2-butane-bis-(N$^1$-trans-3,3-dimethyl-decahydroquinoxalin-2-one having the structure

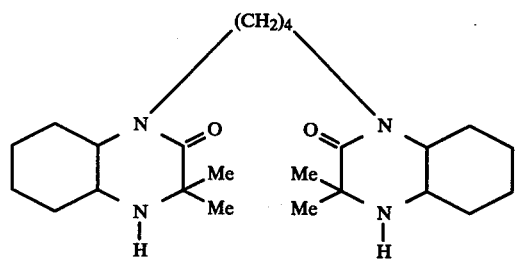

A mixture of cis and trans isomers of 1,2-diaminocyclohexane are dissolved in 500 ml water in a 3-necked flask, and acetone cyanohydrin was slowly added over a period of 45 mins. The mixture is stirred for an additional hour at room temperature, then warmed to 90°–95° C. and maintained at that temperature for 20 hrs. The reaction mixture is then cooled, filtered and the water is removed from the filtrate. Crystals, obtained by recrystallization from acetone, are found to be the trans isomer of 3,3-dimethyl-decahydroquinoxalin-2-one. The melting point of the crystals is about 218.5°–219.5° C.

1.8 g sodium hydride (50% in oil) are placed in a 100 ml flask and 30 ml dried toluene added. After stirring under argon for 5 mins the toluene was pipetted away and 30 ml fresh dry toluene added, followed by 5.5 g trans-3,3-dimethyldecahydroquinoxalin-2-one. The mixture is heated to reflux under argon, while 3.6 g 1,3-dibromobutane in 10 ml toluene are added slowly. The reaction mixture was refluxed overnight, cooled, poured into 60 ml water and extracted with 100 ml benzene. The organic layer is dried over Na$_2$SO$_4$, filtered, and the solvent removed. The oil is triturated with hexane to give 2.5 g of a white solid which melts at 140–4 degrees C.

Elemental analysis calculated: 68.86% C; 13.38% N; 10.11% H. Analysis found: 70.01% C; 13.44% N; 9.92% H.

The structure of the compound is confirmed by IR, NMR and mass spectrometer data.

In a manner analogous to the foregoing, other bis compounds may be prepared; for example, by reaction with α,α'-dibromo-p-xylene instead of dibromobutane, p-xylene-2,2'-bis[N$^1$-(3,3-dimethyl-decahydroquinoxalin-2-one)] is prepared.

EXAMPLE 3

Preparation of 1,1'-(1,2-ethanediyl)bis[4-(2-hydroxyethyl)-3,3,5,5-tetramethyl-2-piperazinone] ("EHTP" for brevity) having the structure

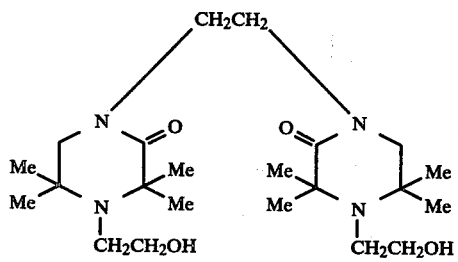

An autoclave (110 ml volume) was charged with 7.05 g (0.021 mole) of 1,1'-(1,2-ethanediyl)bis(3,3,5,5-tetramethyl-2-piperazinone), obtained as described in Example 1 hereinbefore, 40 ml of methanol, 0.2 g of p-toluenesulfonic acid, and 8.8 g (0.2 mole) of ethylene oxide. The reaction was carried out at 150° C. overnight. The resulting solution was cooled and stripped to isolate a semi-solid material which was washed with ethyl acetate to obtain 7.6 g (86% yield) of a compound identified as being one with the above-identified structure, m.p. 166°–179° C.

An analytical sample was obtained by treating the crude product with hot ethyl acetate in which the solid is insoluble, and is isolated by filtration.

Calculated for $C_{22}H_{42}N_4O_4$: C, 61.94; H, 9.93; N, 13.13.

Found: C, 62.12; H, 9.83; N, 13.01.

EXAMPLE 4

A. Preparation of poly[oxycarbonylimino-1,6-hexanediyliminocarbonyloxy-1,2-ethanediyl(2,2,6,6-tetramethyl-3-oxo-1,4-piperazinediyl)-1,2-ethanediyl(3,3,5,5-tetramethyl-2-oxo-1,4-piperazinyl)-1,2-ethanediyl] (identified herein as compound 1), which is formed as a reaction product of 1,1'-(1,2-ethanediyl)bis[4(2-hydroxyethyl)-3,3,5,5-tetramethyl-2-piperazinone] ("EHTP" for brevity), and 1,6-diisocyanatohexane, which reaction product (compound 1) has the structure:

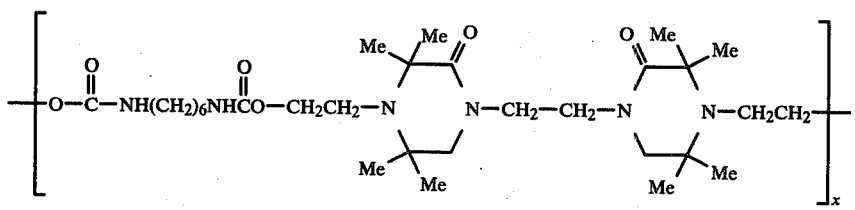

5.55 g (0.013 mole) of EHTP obtained as described hereinabove, 50 ml dry xylene, 0.04 g of 1,4-diazabicyclo[2.2.2]octane and 1.85 g (0.011 mole) hexamethylene diisocyanate are placed in a 100 ml three-necked flask equipped with a mechanical stirrer, condenser and thermometer. The contents of the flask are stirred while gradually heating to reflux under an inert gas (nitrogen) atmosphere. After refluxing overnight, the reaction mixture was cooled. The sticky solid obtained was triturated with hot hexane so as to obtain 7.8 g of straw-colored waxy solid which softens at 65° C. The mol wt of the solid, as shown by vapor pressure osmometry (VPO), is 1230. The value of x is indicated as being about 2.

In a manner analogous with that described in Example 4A hereinabove, other oligomers are obtained as the reaction product of a polysubstituted 2-keto-1,4-diazacycloalkane distally connected to another similar moiety, and, a diisocyanate. Specific such oligomers are obtained as the reaction products of:

B. EHTP and 2,4-diisocyanato-1-methylbenzene which product (compound 2) is identified as p oly[oxycarbonylimino(6-methyl-1,3-phenylene)iminocarbonyloxy-1,2-ethanediyl(2,2,6,6-tetramethyl-3-oxo-1,4-piperazinediyl)-1,2-ethanediyl(3,3,5,5-tetramethyl-2-oxo-1,4-piperazinediyl)-1,2-ethanediyl] having the structure

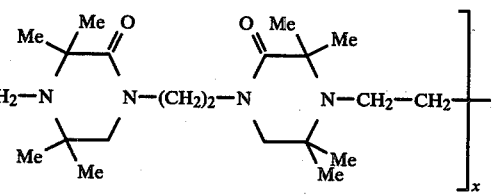

The reaction mixture is heated at 119° C. for several hours and then allowed to continue reaction at room temperature for two days. The resulting light yellow slurry was filtered to isolate a lumpy solid which softens at 200° C.

C. EHTP and 1,1'-methylene-bis[4-isocyanatobenzene] which product (compound 3) is identified as poly[ oxycarbonylimino-1,4-phenylenemethylene-1,4-phenyleneimino-carbonyloxy-1,2-ethanediyl(2,2,6,6-tetramethyl-3-oxo-1,4-piperazinediyl)-1,2-ethanediyl(3,3,5,5-tetramethyl-2-oxo-1,4-piperazinediyl)-1,2-ethanediyl] having the structure

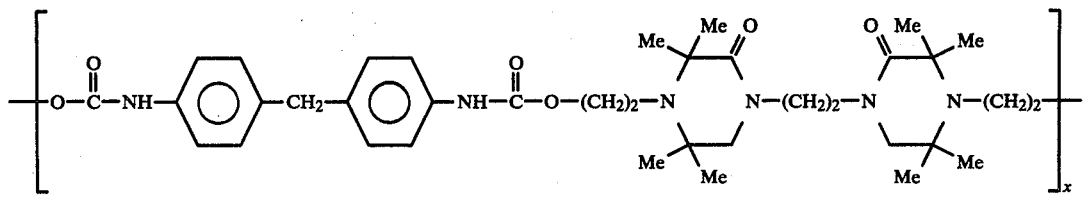

The reaction proceeds at 90°–93° C. overnight, and upon cooling yields an off-white solid which softens at 215° C.

D. EHTP and 5-isocyanato-1-(isocyanatomethyl)-1,3,3-trimethyl-cyclohexane which product (compound 4) is identified as poly[oxycarbonyliminoethylene(1,5,5-trimethyl-1,3-cyclohexanediyl)iminocarbonyloxy-1,2-ethanediyl(2,2,6,6-tetramethyl-3-oxo-1,4-piperazinediyl)-1,2-ethanediyl(3,3,5,5-tetramethyl-2-oxo-1,4-piperazinediyl)-1,2-ethanediyl] having the structure

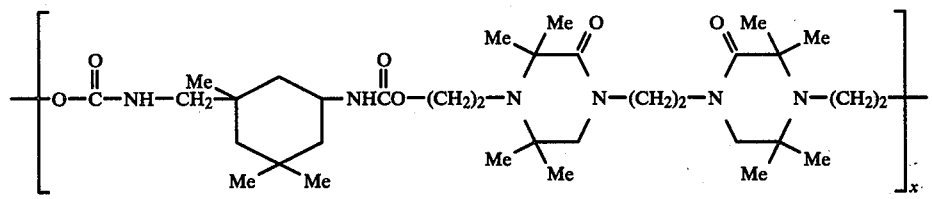

The reaction proceeds at 92°–100° C. overnight and yields a sticky solid which upon trituration with hexane provides a crushable off-white solid softening at 72° C., with a number avg mol wt of 1920 (compound 4).

E. EHTP and 1,1'-methylenebis[4-isocyanatocyclohexane] which product (compound 5) is identified as poly[oxycarbonylimino-1,4-cyclohexanediylmethylene-1,4-cyclohexanediyliminocarbonyloxy-1,2-ethanediyl(2,2,6,6-tetramethyl-3-oxo-1,4-piperazinediyl)-1,2-ethanediyl(3,3,5,5-tetramethyl-2-oxo-1,4-piperazinediyl)-1,2-ethanediyl] having the structure

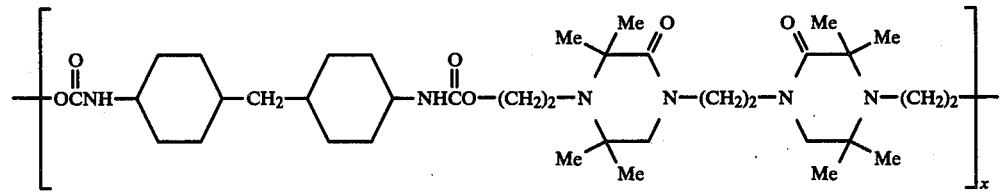

An off-white solid is obtained upon trituration with hexane. The mother liquor was concentrated to a wax to which hexane was added to isolate additional white solid which is combined with that first obtained. The combined solids soften at 74° C. and has a number average mol wt of 1000.

EXAMPLE 5

In a manner analogous to that described in the illustrative examples hereinabove, the following additional reaction products are made:

A. The reaction product of 1,1'(1,4-butanediyl)bis[4-(2-hydroxyethyl)-3,3-dimethyl-trans-decahydroquinoxalin-2-one] and hexamethylene diisocyanate.

B. The reaction product of 1,1'(1,4-butanediyl)bis[4-(2-hydroxyethyl)-3,3-dimethyl-trans-decahydroquinoxalin-2-one] and 5-isocyanato-1-(isocyanatomethyl)-1,3,3-trimethyl cyclohexanone.

C. The reaction product of 1,1'-(1,2-ethanediyl)bis[4-(2-hydroxy-2-methylethyl)-3,3,5,5-tetramethyl-2-piperazinone] and hexamethylene diisocyanate.

D. The reaction product of 1,1'-(1,2-ethanediyl)bis[4-(2-hydroxy-2-methylethyl)-3,3,5,5-tetramethyl-2-piperazinone] and 5-isocyanato-1-(isocyanatomethyl)-1,3,3-trimethyl cyclohexanone.

The following Table I sets forth data obtained in tests conducted with 2 mil thickness samples of polypropylene stabilized with compounds 1–5. The blank and each sample includes 0.05 parts per hundred parts of resin ('phr') of a tri-functional hindered phenol antioxidant available as Goodrite* 3125, and the amount of stabilizer used in each sample is stated. Oven aging is done continuously at 125° C. in the standard test procedure, and the Weather-O-Meter tests give the number of hours after which a sample loses 50% of its tensile strength. These tests were conducted specifically to compare the difficulty with which stabilizer is extracted from polypropylene stabilized with the stabilizer, and the effect of water-extraction of the stabilizer on the time in the Weather-O-Meter when the original tensile strength is reduced by 50%. Water extraction is carried out as follows: A batch of samples are suspended beneath the liquid level in a large flask partially filled with distilled water. The flask is fitted with a reflux condenser and is not open to the atmosphere, so that the water from the flask is not lost. The water is boiled for 24 hours, after which the samples are removed and tested. The results documented in Table I indicate that the samples had comparable oven aging relative to Tinuvin 622 and EHTP, but better tensile strength after water extraction, in spite of the generally high difficulty of extraction of each of the prior art stabilizers.

*Goodrite is a Reg. U.S. Trademark of The B. F. Goodrich Company

TABLE I

| Stabilizer used | Amount stabilizer (phr) | Oven aging (days) | Xenon Weather-O-Meter | |
|---|---|---|---|---|
| | | | Before H₂O extr. | After H₂O extr. |
| | | | (hrs to 50% original tensile) | |
| Tinuvin ® 622 | 0.1 | 26 | 480 | 420 |
| EHTP | 0.1 | 30 | 504 | 344 |
| Compound 1 | 0.1 | 26 | 380 | 180 |
| Compound 2 | 0.1 | 28 | 430 | 280 |
| Compound 3 | 0.1 | 30 | 330 | 220 |
| Compound 4 | 0.1 | 34 | 540 | 520 |
| Compound 5 | 0.1 | 32 | 440 | 480 |

We claim:

1. A class of compounds comprising an oligomer of a 2-keto-1,4-diazacycloalkane and a urethane said oligomer ("2K-U oligomer") having the structure

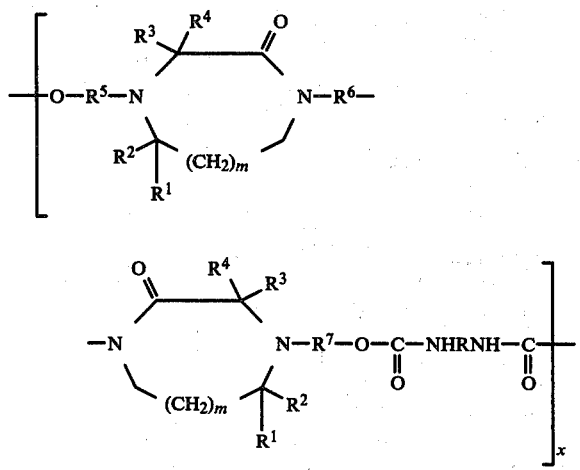

wherein, m represents an integer in the range from 0 to 5, being the number of methylene groups forming a bridge of variable length between the ring N atoms, and some of which groups (a) together with the carbons to which they are bound, may form a cyclopentyl, cyclohexyl or cycloheptyl endo ring, or (b) be substituted; so that, when m is 0, the 2KDZC moiety is a piperazinone ring; when m is 1 the 2KDZC moiety is a 5-keto-1,4-diazacycloheptane ring; when m is 4 and cyclized with the other two contiguous C atoms to form an endo ring, the 2KDZC moiety is decahydroquinoxalinone;

x represents an integer in the range from 2 to about 15;

R is selected from the group consisting of alkylene having from 2 to about 12 carbon atoms, toluyl, diphenylmethyl, naphthyl, dimethyl-biphenyl, dimethoxy-biphenyl, methylcyclohexyl, dicyclohexylmethyl, xylyl, isophoronyl, and trimethylhexyl;

$R^1$, $R^2$, $R^3$ and $R^4$ are independently selected from the group consisting of hydrogen, aryl, alkyl having from 1 to about 24 carbon atoms, cycloalkyl having from 5 to about 7 carbon atoms, aralkyl having from 7 to about 20 carbon atoms, cycloalkyl having from 2 to about 12 carbon atoms, ether having from 4 to about 18 carbon atoms, and hydroxyalkyl having from 1 to about 18 carbon atoms;

$R^1$ and $R^2$ together, or $R^3$ and $R^4$ together, or each pair, may be cyclized forming a ring having from about 5 to about 8 carbon atoms;

except that not more than one of $R^1$, $R^2$, $R^3$ or $R^4$ may be hydrogen, and no more than three of $R^1$, $R^2$, $R^3$ and $R^4$ may be cyclic;

$R^5$ and $R^7$ are each polymethylene having from 2 to about 12 carbon atoms each of which polymethylene constitutes a connecting link distally connecting a 2-keto-diazacycloalkane moiety to a urethane group; and, $R^6$ is selected from the group consisting of polymethylene having from 2 to about 12 carbon atoms, xylenyl substituted or unsubstituted phenyl, which group is a connecting link distally connecting one 2-keto-1,4-diazacycloalkane moiety to another such moiety.

2. The compounds of claim 1 wherein m=0; x represents an integer in the range from about 2 to about 10; and, $R^1$, $R^2$, $R^3$, and $R^4$ are independently selected from lower alkyl having from 1 to about 5 carbon atoms.

3. The compounds of claim 1 wherein m=1; x represents an integer in the range from 2 to about 10; and, $R^1$, $R^2$, R and $R^4$ are independently selected from lower alkyl having from 1 to about 5 carbon atoms.

4. The compounds of claim 1 wherein m=4 and cyclized with the other two C atoms of said bridge to form an endo ring so that each 2KDZC moiety is a polysubstituted decahydroquinoxalinone; x represents an integer in the range from 2 to about 10; and, $R^1$, $R^2$, $R^3$ and $R^4$ are independently selected from lower alkyl having from 1 to about 5 carbon atoms.

5. The compounds of claim 1 wherein $R^5$ and $R^7$ are each polymethylene having from 2 to about 5 carbon atoms.

6. The compounds
poly[oxycarbonylimino-1,6-hexanediyliminocarbonyloxy-1,2-ethanediyl(2,2,6,6-tetramethyl-3-oxo-1,4-piperazinediyl)-1,2-ethanediyl(3,3,5,5-tetramethyl-2-oxo-1,4-piperazinediyl)-1,2-ethanediyl];
poly[oxycarbonylimino(6-methyl-1,3-phenylene)iminocarbonyloxy-1,2-ethanediyl(2,2,6,6-tetramethyl-3-oxo-1,4-piperazinediyl)-1,2-ethanediyl(3,3,5,5-tetramethyl-2-oxo-1,4-piperazinediyl)-1,2-ethanediyl];
poly[oxycarbonylimino-1,4-phenylenemethylene-1,4-phenyleneimino-carbonyloxy-1,2-ethanediyl(2,2,6,6-tetramethyl-3-oxo-1,4-piperazinediyl)-1,2-ethanediyl(3,3,5,5-tetramethyl-2-oxo-1,4-piperazinediyl)-1,2-ethanediyl];
poly[oxycarbonyliminomethylene(1,5,5-trimethyl-1,3-cyclohexanediyl)iminocarbonyloxy-1,2-ethanediyl(2,2,6,6-tetramethyl-3-oxo-1,4-piperazinediyl)-1,2-ethanediyl(3,3,5,5-tetramethyl-2-oxo-1,4-piperazinediyl)-1,2-ethanediyl]; and,
poly[oxycarbonylimino-1,4-cyclohexanediylmethylene-1,4-cyclohexanediyliminocarbonyloxy-1,2-ethanediyl(2,2,6,6-tetramethyl-3-oxo-1,4-piperazinediyl)-1,2-ethanediyl(3,3,5,5-tetramethyl-2-oxo-1,4-piperazinediyl)-1,2-ethanediyl].

7. A composition of matter resistant to degradation by ultraviolet light comprising an organic material subject to ultraviolet light degradation having dispersed therein from about 0.01 part to about 5 parts by weight of a stabilizer compound consisting essentially of a bis compound of a polysubstituted 2-keto-1,4-diazacycloalkane distally linked through the $N^4$ atoms thereof to a urethane moiety, per 100 parts of said organic material, said stabilizer compound being represented by the structural formula

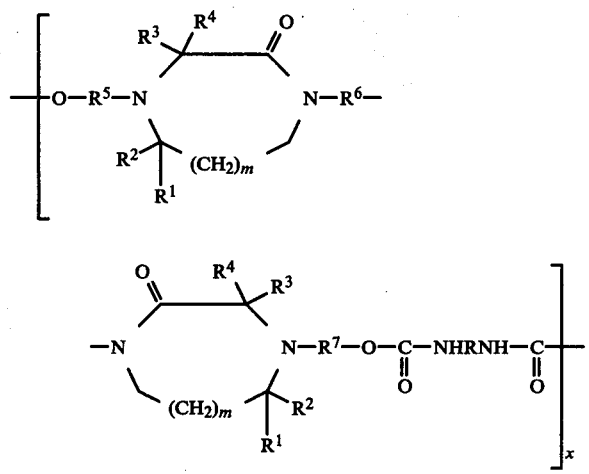

wherein, m represents an integer in the range from 0 to 5, being the number of methylene groups forming a bridge of variable length between the ring N atoms, and some of which groups (a) together with the carbons to which they are bound, may form a cyclopentyl, cyclohexyl or cycloheptyl endo ring, or (b) be substituted; so that, when m is 0, the 2KDZC moiety is a piperazinone ring; when m is 1 the 2KDZC moiety is a 5-keto-1,4-diazacycloheptane ring; when m is 4 and cyclized with the other two contiguous C atoms to form an endo ring, the 2KDZC moiety is decahydroquinoxalinone;

x represents an integer in the range from 2 to about 15;

R is selected from the group consisting of alkylene having from 2 to about 12 carbon atoms, toluyl, diphenylmethyl, naphthyl, dimethyl-biphenyl, dimethoxy-biphenyl, methylcyclohexyl, dicyclohexylmethyl, xylyl, isophoronyl, and trimethylhexyl;

$R^1$, $R^2$, $R^3$ and $R^4$ are independently selected from the group consisting of hydrogen, aryl, alkyl having from 1 to about 24 carbon atoms, cycloalkyl having from 5 to about 7 carbon atoms, aralkyl having from 7 to about 20 carbon atoms, cyanoalkyl having from 2 to about 12 carbon atoms, ether having from 4 to about 18 carbon atoms, and hydroxyalkyl having from 1 to about 18 carbon atoms;

$R^1$ and $R^2$ together, or $R^3$ and $R^4$ together, or each pair, may be cyclized forming a ring having from about 5 to about 8 carbon atoms;

except that not more than one of $R^1$, $R^2$, $R^3$ or $R^4$ may be hydrogen, and no more than three of $R^1$, $R^2$, $R^3$ and $R^4$ may be cyclic;

$R^5$ and $R^7$ are each polymethylene having from 2 to about 12 carbon atoms each of which polymethylene constitutes a connecting link distally connecting a 2-keto-diazacycloalkane moiety to a urethane group; and, $R^6$ is selected from the group consisting of polymethylene having from 2 to about 12 carbon atoms, xylenyl and substituted or unsubstituted phenyl, which group is a connecting link distally connecting one 2-keto-1,4-diazacycloalkane moiety to another such moiety.

8. The composition of claim 7 wherein said stabilizer compound has a structure wherein m=0; x represents an integer in the range from about 2 to about 10; and, $R^1$, $R^2$, $R^3$, and $R^4$ are independently selected from lower alkyl having from 1 to about 5 carbon atoms.

9. The composition of claim 8 wherein said stabilizer compound is selected from the group consisting of
poly[oxycarbonylimino-1,6-hexanediyliminocarbonyloxy-1,2-ethanediyl(2,2,6,6-tetramethyl-3-oxo-1,4-piperazinediyl)-1,2-ethanediyl(3,3,5,5-tetramethyl-2-oxo-1,4-piperazinediyl)-1,2-ethanediyl];
poly[oxycarbonylimino(6-methyl-1,3-phenylene)iminocarbonyloxy-1,2-ethanediyl(2,2,6,6-tetramethyl-3-oxo-1,4-piperazinediyl)-1,2-ethanediyl(3,3,5,5-tetramethyl-2-oxo-1,4-piperazinediyl)-1,2-ethanediyl];
poly[oxycarbonylimino-1,4-phenylenemethylene-1,4-phenyleneimino-carbonyloxy-1,2-ethanediyl(2,2,6,6-tetramethyl-3-oxo-1,4-piperazinediyl)-1,2-ethanediyl(3,3,5,5-tetramethyl-2-oxo-1,4-piperazinediyl)-1,2-ethanediyl];
poly[oxycarbonyliminomethylene(1,5,5-trimethyl-1,3-cyclohexanediyl)iminocarbonyloxy-1,2-ethanediyl(2,2,6,6-tetramethyl-3-oxo-1,4-piperazinediyl)-1,2-ethanediyl(3,3,5,5-tetramethyl-2-oxo-1,4-piperazinediyl)-1,2-ethanediyl]; and,
poly[oxycarbonylimino-1,4-cyclohexanediylmethylene-1,4-cyclohexanediyliminocarbonyloxy-1,2-ethanediyl(2,2,6,6-tetramethyl-3-oxo-1,4-piperazinediyl)-1,2-ethanediyl(3,3,5,5-tetramethyl-2-oxo-1,4-piperazinediyl)-1,2-ethanediyl].

* * * * *

UNITED STATES PATENT AND TRADEMARK OFFICE
CERTIFICATE OF CORRECTION

PATENT NO.  : 4,455,401
DATED       : June 19, 1984
INVENTOR(S) : PYONG NAE SON and JOHN TA-YUAN LAI It is certified that error appears in the above–identified patent and that said Letters Patent are hereby corrected as shown below:

Claim 1, line 62 "cycloalkyl" should read --cyanoalkyl--;

Claim 8, line 2 "m=0" should read --m-=0--.

Signed and Sealed this

Sixth Day of August 1985

[SEAL]

Attest:

DONALD J. QUIGG

Attesting Officer     Acting Commissioner of Patents and Trademarks